United States Patent
Nakajima et al.

(10) Patent No.: US 9,295,489 B2
(45) Date of Patent: Mar. 29, 2016

(54) GUIDE TUBE SYSTEM FOR FORMING PNEUMOPERITONEUM AND PROVIDING ROUTE FOR ACCESSING BODY CAVITY

(75) Inventors: Kiyokazu Nakajima, Osaka (JP); Toshirou Nishida, Osaka (JP); Tsuyoshi Takahashi, Osaka (JP); Yoshihito Souma, Osaka (JP)

(73) Assignee: Osaka University, Osaka (JP)

( * ) Notice: Subject to any disclaimer, the term of this patent is extended or adjusted under 35 U.S.C. 154(b) by 743 days.

(21) Appl. No.: 13/144,139

(22) PCT Filed: Jan. 20, 2010

(86) PCT No.: PCT/JP2010/050602
§ 371 (c)(1),
(2), (4) Date: Jul. 12, 2011

(87) PCT Pub. No.: WO2010/084869
PCT Pub. Date: Jul. 29, 2010

(65) Prior Publication Data
US 2011/0282138 A1  Nov. 17, 2011

(30) Foreign Application Priority Data
Jan. 21, 2009  (JP) ................. 2009-010595

(51) Int. Cl.
*A61M 37/00* (2006.01)
*A61M 1/00* (2006.01)
(Continued)

(52) U.S. Cl.
CPC ......... *A61B 17/3474* (2013.01); *A61B 17/3403* (2013.01); *A61B 17/3415* (2013.01);
(Continued)

(58) Field of Classification Search
CPC .... A61B 1/00087; A61B 1/012; A61B 1/015; A61B 1/018; A61B 1/12; A61B 1/313; A61B 1/3132; A61B 17/3401; A61B 17/3415; A61B 17/3403; A61B 17/3474; A61B 17/3478; A61B 17/3494; A61B 17/3496; A61B 17/34

USPC ......... 600/104, 106, 114–115, 156–159, 560; 604/23, 26, 27, 43–45, 164.01–164.13, 604/506; 606/108, 185
See application file for complete search history.

(56) References Cited

U.S. PATENT DOCUMENTS 5,029,588 A *  7/1991  Yock et al. ............ 600/471
5,098,388 A *  3/1992  Kulkashi et al. ........ 604/158
(Continued)

FOREIGN PATENT DOCUMENTS

JP          8507238       8/1996
JP       2004-329763    11/2004
(Continued)

OTHER PUBLICATIONS

PCT/JP2010/050602; PCT International Search Report dated Mar. 10, 2010.
(Continued)

*Primary Examiner* — Ryan Henderson
(74) *Attorney, Agent, or Firm* — Renner, Otto, Boisselle & Sklar, LLP (57) ABSTRACT

The guide tube for forming a pneumoperitoneum of the present invention comprising a flexible tube having an inner cavity, has an outer diameter that allows the guide tube to be inserted into a puncture needle, a distal end of the guide tube is closed, the distal end is provided with a tip portion that can be held by holding forceps provided in an endoscope, a proximal end of the guide tube is provided with a connecting portion to an insufflation apparatus, and the guide tube is provided with a side hole region having at least one side hole that can establish communication between the inner cavity of the flexible tube and the outside in a case where the inner cavity is pressurized through insufflation. According to the guide tube for forming a pneumoperitoneum of the present invention, only with single puncture from the body surface into the lumen of a lumen organ, a preliminary pneumoperitoneum can be safely and reliably created without damaging other organs, and, at the same time, the part of the lumen organ wall pierced during formation of the pneumoperitoneum can be used as a route for accessing the peritoneal cavity from the lumen of the lumen organ.

13 Claims, 6 Drawing Sheets

(51) Int. Cl.
- *A61M 5/178* (2006.01)
- *A61M 31/00* (2006.01)
- *A61F 11/00* (2006.01)
- *A61B 17/34* (2006.01)
- *A61B 1/00* (2006.01)
- *A61B 17/29* (2006.01)
- *A61B 17/00* (2006.01)
- *A61B 19/00* (2006.01)
- *A61M 25/00* (2006.01)
- *A61J 15/00* (2006.01)

(52) U.S. Cl.
CPC ...... *A61B 17/29* (2013.01); *A61B 2017/00278* (2013.01); *A61B 2019/462* (2013.01); *A61J 15/0007* (2013.01); *A61M 25/007* (2013.01)

(56) References Cited

U.S. PATENT DOCUMENTS

| | | | |
|---|---|---|---|
| 5,320,611 A | | 6/1994 | Bonutti et al. |
| 5,374,252 A | * | 12/1994 | Banks et al. ............ 604/158 |
| 5,431,676 A | | 7/1995 | Dubrul et al. |
| 6,309,345 B1 | * | 10/2001 | Stelzer et al. ............ 600/106 |
| 6,494,893 B2 | * | 12/2002 | Dubrul et al. ............ 606/185 |
| 2005/0277945 A1 | | 12/2005 | Saadat et al. |
| 2007/0163585 A1 | | 7/2007 | Uesugi et al. |
| 2007/0167967 A1 | | 7/2007 | Mikkaichi et al. |
| 2007/0255165 A1 | | 11/2007 | Uesugi et al. |
| 2007/0255303 A1 | | 11/2007 | Bakos et al. |
| 2007/0260273 A1 | | 11/2007 | Cropper et al. |
| 2008/0004566 A1 | * | 1/2008 | Sloan ............................ 604/30 |
| 2008/0275383 A1 | * | 11/2008 | Weisel et al. ............. 604/35 |
| 2009/0326560 A1 | * | 12/2009 | Lampropoulos et al. ..... 606/148 |

FOREIGN PATENT DOCUMENTS

| | | |
|---|---|---|
| JP | 2007296349 | 11/2007 |
| JP | 2007301364 | 11/2007 |
| JP | 2008502421 | 1/2008 |
| WO | 2007080971 | 7/2007 |
| WO | 2007081056 | 7/2007 |

OTHER PUBLICATIONS

C.W. Ko et al., "Preliminary pneumoperitoneum facilitates transgastric access into the peritoneal cavity for natural orifice transluminal endoscopic surgery: A pilot study in a live porcine model", Endoscopy, 2007, vol. 39, pp. 849-853.

E. Sporn et al., "Gastrotomy creation and closure for NOTES using a gastropexy technique (with video)", Gastrointestinal Endoscopy, 2008, vol. 68(5), 948-953.

J.M. Marks et al., "PEG "Rescue": a pratical NOTES technique"; Surg Endosc., 2007, vol. 21(5), 816-819.

* cited by examiner

Fig. 1 side hole region

Fig. 2 insufflation

GUIDE TUBE SYSTEM FOR FORMING PNEUMOPERITONEUM AND PROVIDING ROUTE FOR ACCESSING BODY CAVITY

TECHNICAL FIELD

The present invention relates to a guide tube for forming a pneumoperitoneum. More specifically, the present invention relates to a guide tube for forming a pneumoperitoneum only with single puncture from the body surface without performing improper puncture, and, at the same time, for providing a route for accessing a body cavity, and a system for forming a pneumoperitoneum and a method for forming a pneumoperitoneum using the same.

BACKGROUND ART

In clinical departments, direct observations or procedures in a body cavity are performed in order to diagnose various disease states, see treatment effects, determine treatment policies, and the like. Conventionally, these operations have been performed with a very invasive approach such as exploratory laparotomy or exploratory thoracotomy. However, as endoscopic surgeries are recently becoming widely carried out, these are performed using an exploratory laparoscope or an exploratory thoracoscope in which the size of incisional wounds is smaller than that in conventional examples.

For example, Patent Documents 1 and 2 disclose trocar systems that, after being inserted into a body cavity by piercing the skin to form a hole having a small diameter, can easily increase the diameter of the through hole to provide a route for passing a surgical tool having a larger diameter. According to these systems, the size of an external wound of a patient is smaller and the recovery time is extremely shorter than those in conventional examples where a large incision according to the diameter of a surgical tool is made.

Meanwhile, a new minimally-invasive technique for suppressing an external wound of a patient to the extent possible is developed. This technique is known as Natural Orifice Translumenal Endoscopic Surgery (NOTES), and is a completely new technique that inserts a flexible endoscope from an orifice on the body surface (natural orifice: mouth, anus, vagina, etc.) of a lumen organ into the lumen, makes an incision or a perforation through the lumen organ wall to access a body cavity, and makes a diagnosis or performs procedures or treatment. Theoretically, this technique needs no incisional wound on the body surface (incisionless), and, thus, the invasiveness thereof is expected to be lower than that of an endoscopic surgery. In a foreign country, a successful clinical case of laparoscope-assisted transvaginal or transgastric "hybrid NOTES" is reported, and has been attracting great attention. In near future, non-laparoscope-assisted "pure NOTES" only with a flexible endoscope is expected to be introduced to clinical practice.

Various tools or apparatuses for use in such NOTES are developed (Patent Documents 3 and 4). For example, Patent Document 3 discloses a translumenal trocar tool, including an elongated flexible trocar sleeve and an elongated flexible obturator that is disposed through the trocar sleeve. It is described that, in this tool, a distal end portion of the obturator has means for facilitating tissue penetration of the distal end portion. However, this tissue penetrating means uses a blade as a cutting unit, and, when this tool is used, an incision is made through the lumen. Furthermore, also in an apparatus disclosed in Patent Document 4, a puncturing unit is configured to breach the wall of a body organ.

One of technical demands in such NOTES is to safely create a route for accessing a body cavity. In the case of a transgastric route as an example, it is necessary to minimize the risk of damaging adjacent organs to the extent possible when making an incision or a perforation through the stomach wall. Thus, "preliminary pneumoperitoneum method" is proposed that, before making an incision or a perforation through the stomach wall in NOTES, makes a puncture from the body surface into the peritoneal cavity using a pneumoperitoneum needle having a small diameter, and injects carbon dioxide in advance into the peritoneal cavity (Non-Patent Document 1). According to this approach, a space is formed between the stomach and adjacent organs, and, thus, the risk of damaging the adjacent organs when making an incision or a perforation through the stomach wall is significantly reduced. However, the operation of creating a preliminary pneumoperitoneum is a conventional blind puncture operation using a pneumoperitoneum needle, and, thus, this operation itself has a risk of inducing complications such as improper puncture of intraperitoneal organs.

PRIOR ART DOCUMENTS

Patent Documents

Patent Document 1: U.S. Pat. No. 5,320,611
Patent Document 2: Japanese National Publication No. 8-507238
Patent Document 3: Japanese Laid-Open Patent Publication No. 2007-301364
Patent Document 4: Japanese National Publication No. 2008-502421

Non-Patent Documents

Non-Patent Document 1: Ko C W et al., Endoscopy, 2007, vol. 39, pp. 849-853

SUMMARY OF INVENTION

Problems to be Solved by the Invention

In this manner, for example, in NOTES, safe creation of a route for accessing a body cavity is one of study subjects to which the highest priority has to be given. Thus, it is an object of the present invention to provide means and approach for safely and reliably creating a preliminary pneumoperitoneum.

Means for Solving the Problems

The present invention has been achieved by finding that it is possible to safely and reliably create a preliminary pneumoperitoneum by combining the concept of "percutaneous endoscopic gastrostomy (PEG)" currently widely used in clinical practice with the above-described "preliminary pneumoperitoneum method".

The present invention provides a guide tube for forming a pneumoperitoneum comprising a flexible tube having an inner cavity,
   wherein the guide tube has an outer diameter that allows the guide tube to be inserted into a puncture needle,
   a distal end of the guide tube is closed, and the distal end is provided with a tip portion that can be held by holding forceps provided in an endoscope,
   a proximal end of the guide tube is provided with a connecting portion to an insufflation apparatus, and the guide tube is provided with a side hole region having at least one side hole that can establish communication between the inner cavity of the flexible tube and the outside in a case where the inner cavity is pressurized through insufflation.

In one embodiment, an outer surface of the guide tube is provided with at least one marker.

In a further embodiment, an outer surface of the guide tube is provided with markers at points of a distal side and a proximal side of the side hole region.

In an embodiment, the side hole region has a length of 7 cm to 15 cm.

In other embodiment, the puncture needle has a size of 14 G to 18 G.

The present invention also provides a system for forming a pneumoperitoneum, comprising:
any one of the guide tube; and
a puncture needle having a length that allows the puncture needle to penetrate a body surface into a target lumen.

In one embodiment, the system for forming a pneumoperitoneum further comprises an insufflation apparatus.

In an embodiment, the system for forming a pneumoperitoneum further comprises an endoscope, wherein the endoscope is provided at least with an observation optical system, an illumination optical system, holding forceps, and insufflation and suction means.

The present invention further provides a method for forming a pneumoperitoneum, comprising the steps of:
inserting an endoscope into a lumen of a lumen organ of a subject;
causing a puncture needle to penetrate a body surface of the subject into the lumen under observation using the endoscope;
inserting a distal end of the guide tube of any one of claims 1 to 5 through an inner cavity of the puncture needle into the lumen;
holding the distal end with holding forceps provided in the endoscope;
extracting the puncture needle, and positioning at least one side hole of the guide tube in a peritoneal cavity; and injecting a gas via the side hole of the guide tube into the peritoneal cavity.

In one embodiment, the lumen organ is a stomach.

In an embodiment, any one of the said system for forming a pneumoperitoneum is used in the method.

The present invention also provides a method for providing a route for accessing a body cavity from a lumen of a lumen organ, comprising the steps of:
inserting an endoscope into the lumen of the lumen organ of a subject;
causing a puncture needle to penetrate a body surface of the subject into the lumen under observation using the endoscope;
inserting a distal end of the guide tube of any one of claims 1 to 5 through an inner cavity of the puncture needle into the lumen;
holding the distal end with holding forceps provided in the endoscope;
extracting the puncture needle, and positioning at least one side hole of the guide tube in the body cavity;
injecting a gas via the side hole of the guide tube into the body cavity;
pulling the guide tube in a proximal direction, and guiding lumen wall piercing means provided in the endoscope to a wall of the lumen; and
providing a route for accessing the body cavity through the wall of the lumen with the lumen wall piercing means.

Effects of Invention

According to the guide tube of the present invention, only with single puncture from the body surface into the lumen of a lumen organ (e.g., into the stomach), not only a preliminary pneumoperitoneum is formed, but the part of the lumen organ wall pierced during formation of the pneumoperitoneum can be used as a route for accessing the peritoneal cavity from the lumen of the lumen organ. In this manner, according to the present invention, for example, puncture into the stomach is performed under observation using an endoscope, and, thus, damage to organs can be avoided, and the safety is higher than that in blind puncture into the peritoneal cavity. Almost all techniques are realized as simple operations that are the same as those in percutaneous endoscopic gastrostomy (PEG) already widely used in clinical practice, and, thus, a preliminary pneumoperitoneum can be safely and reliably created.

MODE FOR CARRYING OUT THE INVENTION

Prior to a description of the present invention, a definition of terms will be given.

In this specification, the term "proximal" refers to a part of the tool situated closest to an operator of the tool, and the term "distal" refers to a part of the tool situated farthest from the operator.

In the present invention, "incision" and "puncture" refer to mutually different operations. "Incision" refers to an operation that cuts through tissue with a blade (or a knife). On the other hand, "puncture" refers to an operation that forms a hole using a pointed tool such as a needle, and this hole is formed by pushing apart fibers of tissue in the direction of the fibers without making an incision through the tissue.

The guide tube for forming a pneumoperitoneum of the present invention is a hollow guide tube having a small diameter that allows the guide tube to be inserted into a puncture needle, and has a side hole. More specifically, the guide tube for forming a pneumoperitoneum of the present invention has the feature that the guide tube is composed of a flexible tube having an inner cavity, has an outer diameter that allows the guide tube to be inserted into a puncture needle, a distal end of the guide tube is closed, the distal end is provided with a tip portion that can be held by holding forceps provided in an endoscope, a proximal end of the guide tube is provided with a connecting portion to an insufflation apparatus, and the guide tube is provided with a side hole region having at least one side hole that can establish communication between the inner cavity of the flexible tube and the outside in a case where the inner cavity is pressurized through insufflation.

The distal end of the flexible tube constituting the guide tube of the present invention is closed, and the distal end is provided with a tip portion that can be held by holding forceps provided in an endoscope. The tip portion has a diameter and a strength that allow the tip portion to be partially pulled into the endoscope after being held by the holding forceps. The tip portion is made of, for example, a stainless steel wire. The diameter or width of the tip portion may be typically approximately 10 μm to 500 μm, preferably approximately 100 μm to 300 μm, and more preferably approximately 200 μm. There is no particular limitation on the cross-sectional shape of the tip portion, and examples thereof include a circle and a quadrangle. There is no particular limitation on the length of the tip portion, but it is preferably a length that allows the tip portion to be sufficiently pulled into the endoscope. The length may be preferably approximately 0.5 m to 5 m, more preferably approximately 2 m to 4 m, and even more preferably approximately 3 m.

The proximal end of the flexible tube constituting the guide tube of the present invention is provided with a connecting portion to an insufflation apparatus. There is no particular limitation on the shape of the connecting portion, and any shape is applicable as long as it matches a connecting portion provided in an insufflation port of an insufflation apparatus used. The connecting portion of the guide tube preferably has a shape that matches a connecting system in which the guide tube is not detached even when the inner cavity of the guide tube is pressurized through insufflation, and examples of such connecting system preferably include Luer lock system. The connecting portion may be made of a material ordinarily used for connection of medical tools, and examples thereof include polyethylene, polyester, and polyamide.

There is no particular limitation on the length of the flexible tube constituting the guide tube of the present invention as long as it is a length that causes no trouble in connection to the insufflation apparatus and that does not inhibit formation of a pneumoperitoneum. The length may be preferably approximately 0.3 m to 1.5 m, more preferably approximately 0.5 m to 1.0 m. Furthermore, the outer diameter of the flexible tube constituting the guide tube of the present invention is determined according to the size of a puncture needle used. Any outer diameter is applicable as long as it allows the guide tube to pass through the puncture needle. In the present invention, a puncture needle having a size of 14 G to 18 G may be preferably used.

The flexible tube constituting the guide tube of the present invention is provided with a side hole region having at least one side hole that can establish communication between the inner cavity and the outside in a case where the inner cavity is pressurized through insufflation. The size and the number of side holes may be set as appropriate according to the material and the size of the guide tube such that the guide tube is not broken even when the guide tube is pulled in the distal end direction or the proximal end direction.

At least one side hole is provided in the side hole region. A distal end of the side hole region is positioned so as to be away from the tip portion of the guide tube inserted into a target lumen (e.g., the stomach) at least by the distance equivalent to the thickness of the lumen wall. The distal end of the side hole region is preferably positioned so as to be away from the proximal end of the tip portion at least by 1 cm. Furthermore, the length of the side hole region of the guide tube may be preferably 7 cm to 15 cm, more preferably approximately 10 cm.

Furthermore, an outer surface of the guide tube for forming a pneumoperitoneum of the present invention preferably has at least one marker. This marker may be provided in order to check the position of the side hole region using an endoscope or visually. For example, the marker may be disposed at a point of the distal side of the side hole region such that it is possible to confirm that the side hole of the guide tube is positioned in the peritoneal cavity by checking the marker with the endoscope. Markers are more preferably arranged so as to sandwich the side hole region, that is, at both points of the distal side and the proximal side of the side hole region. Alternatively, a plurality of marker may be arranged at constant intervals on the outer surface of the side hole region.

The flexible tube constituting such a guide tube is made of a material ordinarily used for medical tools, and, for example, needs to be flexible, be strong, cause less friction (be smooth), and have column stiffness. Examples of such a material include silicone rubber and polytetrafluoroethylene (PTFE). Further examples thereof include a flexible material used for a stent and the like. For example, medical stainless steel, such as 316L stainless steel, tantalum, cobalt alloy, nitinol (nickel-titanium alloy), and the like may be used. The outer surface of these materials may be coated with a porous polytetrafluoroethylene (ePTFE) film, a silicone film, a polyurethane film, a Dacron film, or the like.

Figure 1:
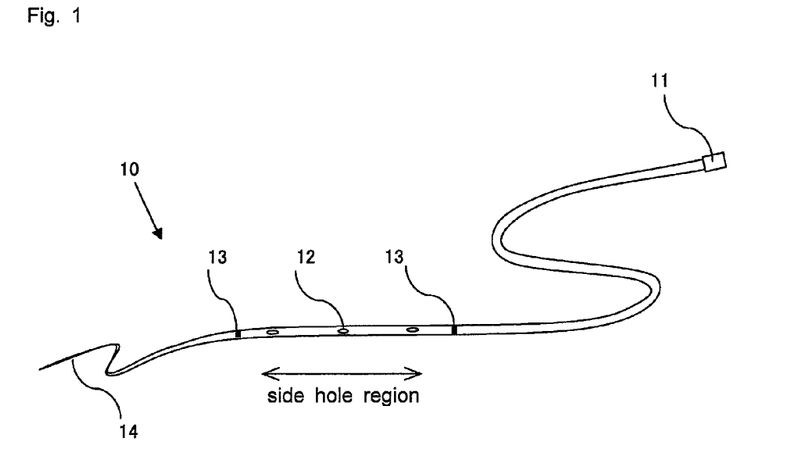
FIG. 1 is a schematic view showing an embodiment of the structure of a guide tube for forming a pneumoperitoneum of the present invention.

FIG. 1 is a schematic view showing an embodiment of the structure of a guide tube 10 for forming a pneumoperitoneum of the present invention. The guide tube 10 is hollow, that is to say, has an inner cavity. A distal end of the guide tube is closed, and is provided with a tip portion 14 that can be held by holding forceps provided in an endoscope. Meanwhile, a proximal end thereof is provided with a connecting portion 11 to an insufflation apparatus (not shown). The flexible tube constituting the guide tube 10 has, for example, a plurality of side holes 12. On the outer surface of the guide tube 10, two markers 13 are arranged so as to sandwich the region where the side holes 12 are present (side hole region).

The system for forming a pneumoperitoneum of the present invention is provided with the above-described guide tube and a puncture needle. The puncture needle has a length that allows the puncture needle to penetrate the body surface into a target lumen. As described above, the puncture needle preferably has a size of 14 G to 18 G.

The system for forming a pneumoperitoneum of the present invention is further provided with an insufflation apparatus. As the insufflation apparatus, an insufflation apparatus for medical use (e.g., for an endoscope) is typically used. Such an insufflation apparatus can keep the pressure of a gas in a closed space proper based on an electrical signal according to the pressure detected by a pressure sensor, in order to adjust the amount of air (or carbon dioxide) supplied from the closed space of the insufflation apparatus (insufflation amount). The insufflation amount is set as appropriate according to the size or the number of side holes of the guide tube, the strength of a material of the flexible tube of the guide tube, and the like. For example, if the flow rate is 20 to 30 L/min, the peritoneal cavity is immediately expanded. Even if the flow rate is approximately 1 L/min, the peritoneal cavity can be sufficiently expanded.

The system for forming a pneumoperitoneum of the present invention is further provided with an endoscope. In the present invention, "endoscope" refers to a flexible endoscope for medical use unless otherwise described. Such a flexible endoscope is made of a flexible material, and an observation optical system embedded therein may be of a glass fiber type or of a CCD type. Typically, an illumination optical system is provided with a light source on the controller side outside the body, and guides light through optical fibers and emits the light from an end portion of the illumination optical system. Furthermore, an LED may be embedded in an end of the endoscope. Typically, an endoscope has a path (sub lumen or channel) other than these optical systems, and can, for example, wash a local portion, inject gas or liquid, apply a drug, perform suction, and perform procedures (holding, cutting, puncture, etc.) using a dedicated device. Furthermore, the orientation of the end of the endoscope can be freely changed by operation at hand.

In the present invention, an endoscope is used that is provided at least with an observation optical system, an illumination optical system, holding forceps, and insufflation and suction means. As the endoscope, an endoscope having an appropriate size is selected according to a lumen organ into which the endoscope is to be inserted. Examples of the lumen organ include the stomach, the small intestine, the large intestine, the vagina, and the bladder. Particularly preferably, the endoscope is used for the stomach.

The guide tube of the present invention, being encased in the puncture needle, is inserted through the abdominal wall once into a lumen of a lumen organ, and held and secured by the endoscope. Subsequently, the guide tube can create a preliminary pneumoperitoneum through insufflation of carbon dioxide from the side holes positioned in the peritoneal cavity into the peritoneal cavity. The guide tube of the present invention may be used also as, for example, a guide for forming a transgastric route from the inside of the stomach to the peritoneal cavity after creating a preliminary pneumoperitoneum.

A specific method for using the guide tube for forming a pneumoperitoneum and the system for forming a pneumoperitoneum (i.e., method for forming a pneumoperitoneum) of the present invention will be specifically described using the case of transgastric NOTES as an example with reference to the drawings.

Figure 2:
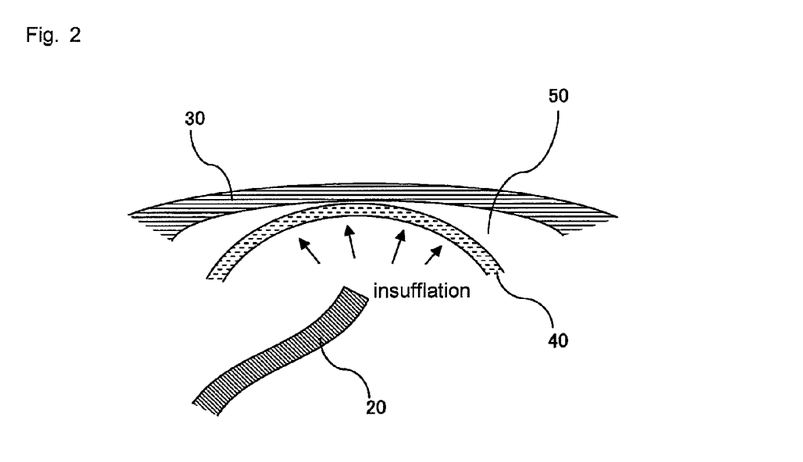
FIG. 2 is an explanatory view showing a state in which an endoscope is inserted into the stomach, the stomach is expanded through insufflation of carbon dioxide from the endoscope, and, thus, the stomach wall is brought into contact with the abdominal wall.
Figure 3:
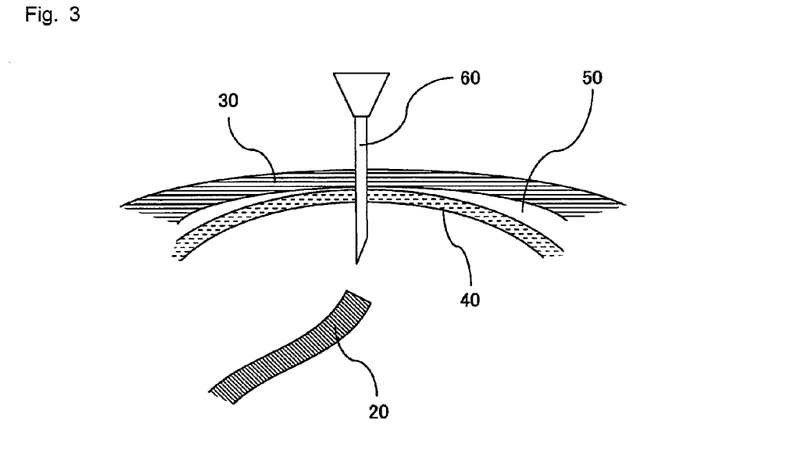
FIG. 3 is an explanatory view showing a state in which a puncture needle penetrates a portion where the abdominal wall and the stomach wall are in contact with each other.

An endoscope 20 is inserted through the mouth into the stomach, the stomach is expanded through insufflation via the endoscope 20, and, thus, a stomach wall 40 is brought into contact with an abdominal wall 30 (see FIG. 2). Next, the endoscope 20 is brought closer to the stomach wall 40 at a point where the stomach wall 40 and the abdominal wall 30 are in contact with each other, and the illumination optical system of the endoscope is caused to emit light from the end. The light from the endoscope 20 can be visually seen from the body surface. Accordingly, toward the light, under observation using the endoscope 20, a puncture needle 60 is caused to penetrate, from the body surface, the abdominal wall 30 and the stomach wall 40, and is directly inserted into the stomach (see FIG. 3). The above-described operation is a commonly performed approach in PEG.

Figure 4:
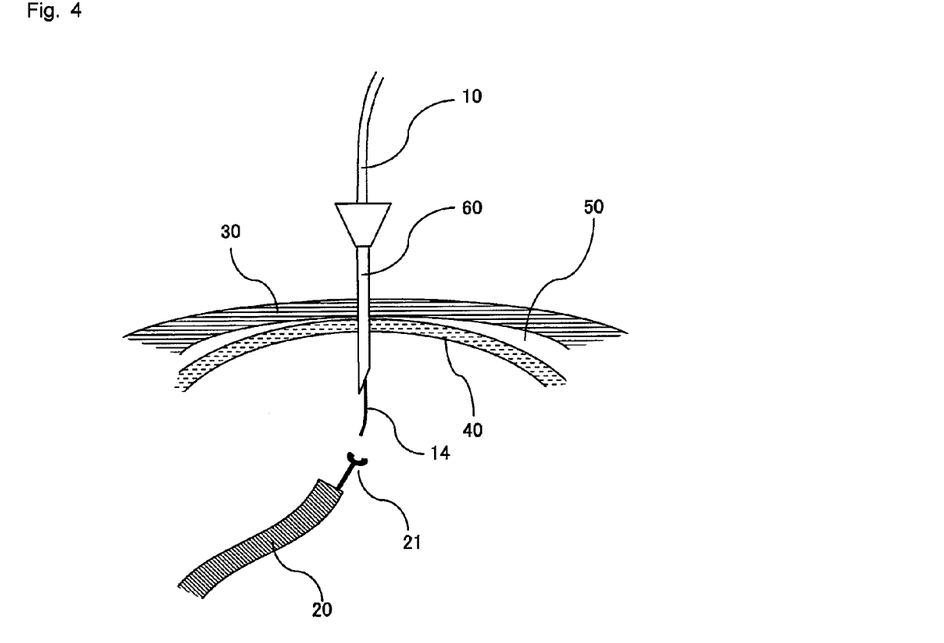
FIG. 4 is an explanatory view showing a state in which a tip portion of the guide tube is inserted through the penetrating puncture needle into the stomach, and holding forceps are projected from the endoscope.
Figure 5:
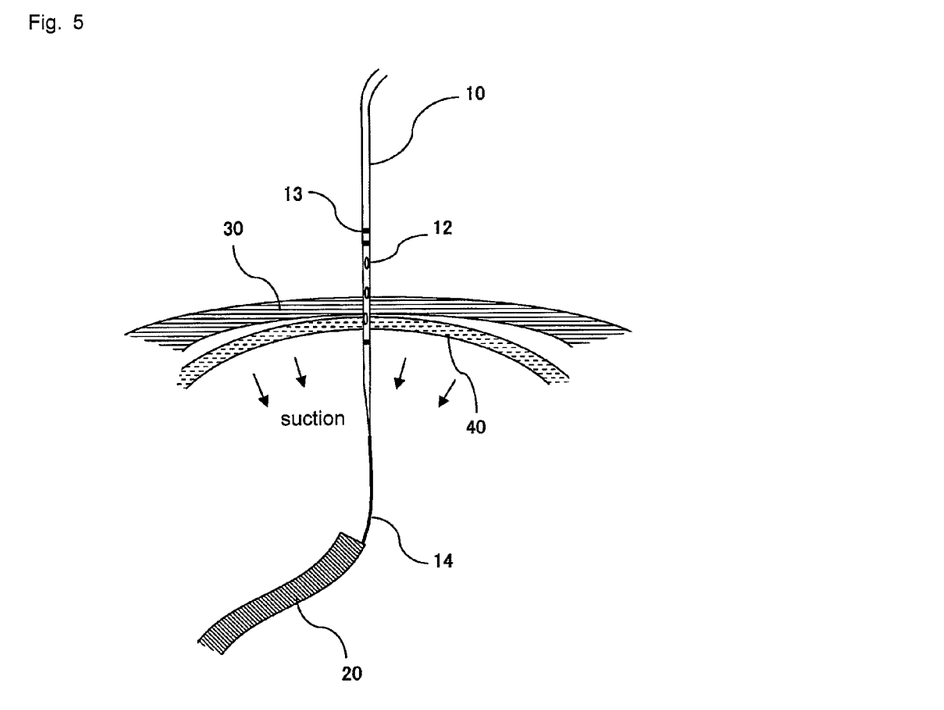
FIG. 5 is an explanatory view showing a state in which the tip portion of the guide tube is secured in the endoscope, the puncture needle is extracted out of the body, suction of gas in the stomach using the endoscope is started, and the stomach begins to be contracted.

Next, the guide tube 10 of the present invention is inserted through the puncture needle 60 into the stomach, and the tip portion 14 of the guide tube is held by holding forceps 21 of the endoscope (see FIG. 4). After part of the tip portion 14 held by the holding forceps 21 is pulled into the endoscope 20 and secured, the puncture needle 60 is extracted out of the body (see FIG. 5). Next, suction is performed in the stomach through the endoscope 20 to reduce the pressure (see FIG. 5). Accordingly, the stomach is contracted, and a space is formed between the stomach wall 40 and the abdominal wall 30. At least approximately 2 to 3 cm is sufficient in order to perform the following operation as the distance between the stomach wall 40 and the abdominal wall 30.

Figure 6:
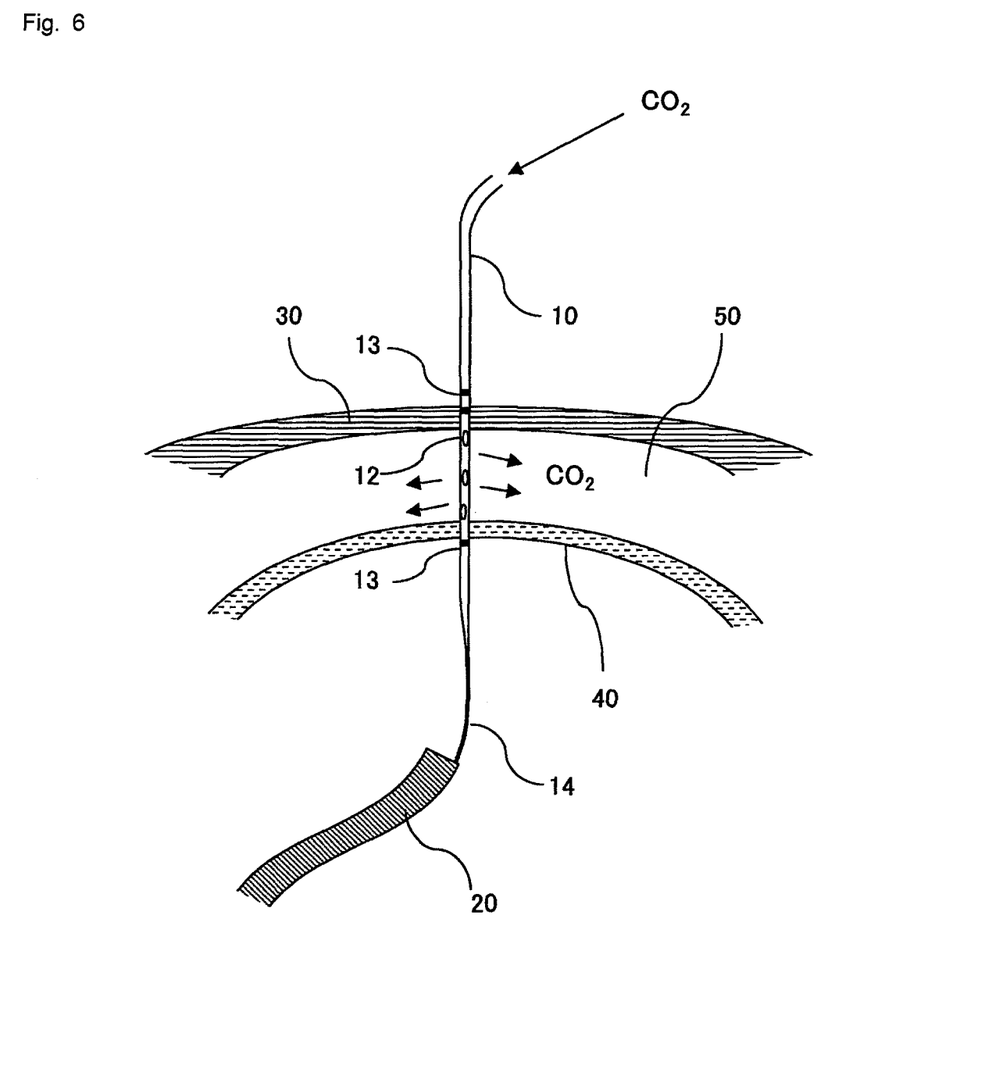
FIG. 6 is an explanatory view showing a state in which suction of gas in the stomach using the endoscope ends, the position of the guide tube is adjusted such that a distal-most marker of the guide tube is in the stomach and a predetermined proximal marker disappears from sight on the body surface, insufflation of carbon dioxide from side holes of the guide tube into the peritoneal cavity is started, and the peritoneal cavity begins to be expanded.

Next, under observation using the endoscope 20, the tip portion 14 of the guide tube is pulled by the endoscope 20, and, thus, adjustment is performed such that the plurality of side holes 12 provided on the guide tube 10 are positioned in a peritoneal cavity 50 (see FIG. 6). At that time, it is possible to confirm that the side holes 12 are positioned in the peritoneal cavity 50, by checking with the endoscope 20 a distal-most marker among the markers 13 on the outer surface of the guide tube 10. Here, there is no problem even if part of the side holes is present in the stomach. For example, in the case where the stomach is expanded through insufflation via the guide tube into the stomach, suction can be performed using the endoscope. Furthermore, if a marker is provided at a point of the proximal side of the side hole region, it is possible to confirm that the side holes are positioned in the peritoneal cavity when this marker disappears from sight on the body surface. Here, the abdominal wall includes a large number of layers such as the skin, the subcutaneous tissue, the abdominal muscle, and the peritoneal membrane, and, thus, it is not preferable that a side hole is positioned in the abdominal wall. Accordingly, a plurality of markers are preferably provided at constant intervals at a point of the proximal side of the side hole region. In this case, adjustment can be performed such that no side hole is positioned in the abdominal wall according to the thickness of the abdominal wall of a subject, by visually seeing the markers.

Figure 7:
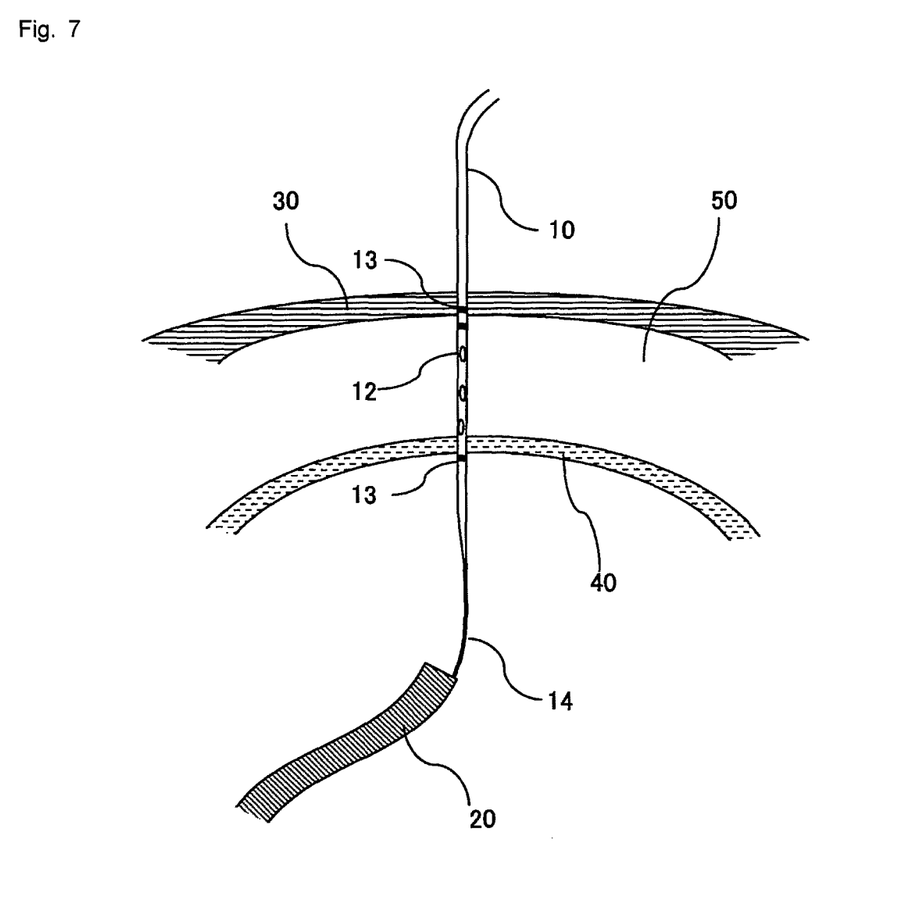
FIG. 7 is an explanatory view showing a state in which insufflation of carbon dioxide from the side holes of the guide tube into the peritoneal cavity ends, and the peritoneal cavity has been expanded.

Next, the proximal end of the guide tube 10 is connected to a carbon dioxide insufflation apparatus, and carbon dioxide is injected from the side holes 12 of the guide tube into the peritoneal cavity 50 (see FIGS. 6 and 7). In this manner, according to the guide tube of the present invention, it is possible to safely and reliably form a pneumoperitoneum with single puncture (preliminary pneumoperitoneum method).

Next, using lumen wall piercing means (e.g., a balloon catheter, a needle-type electric scalpel, etc.) provided in the endoscope, a route for accessing the peritoneal cavity from the inside of the stomach is created along the guide tube. This operation is the same as that in currently performed transgastric NOTES, but is different therefrom in that there is a guide tube that guides a route for accessing the peritoneal cavity. Accordingly, a route for accessing the peritoneal cavity can be created without requiring the aid of a laparoscope. For example, in the case where holding forceps are provided in an end of a balloon catheter, the balloon catheter can be moved forward along the route of the guide tube to the stomach wall by pulling the guide tube in the proximal direction. By inflating a balloon when this balloon catheter pierces the stomach wall, a route for accessing the peritoneal cavity from the inside of the stomach can be created. Alternatively, a route for accessing the peritoneal cavity can be created, for example, by making an incision through the stomach wall using a needle-type electric scalpel along the guide tube. After creating the access route, the guide tube can be extracted, and any tool such as an endoscope or a catheter can be inserted.

Examples

Figure 8:
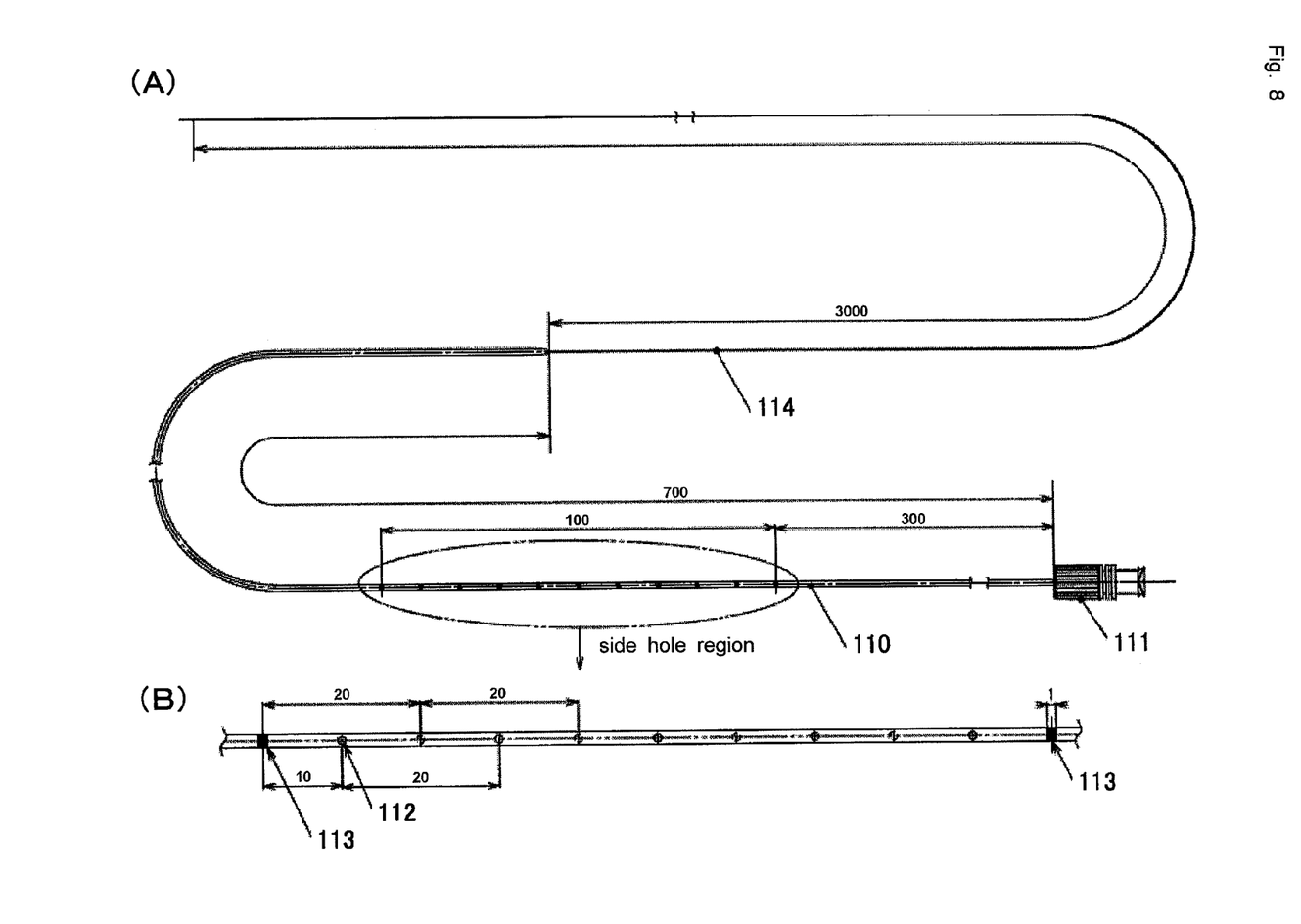
FIG. 8(A) is a front view of a guide tube used in an animal experiment.
FIG. 8(B) is an enlarged view of a side hole region.

FIG. 8(A) shows a front view of a guide tube 110 used in an animal experiment. The unit of values indicating the distances defined by the double-ended arrows in FIG. 8 is "mm". A tip portion 114 of the guide tube 110 was configured from a stainless steel tube having an outer diameter of 0.21 mm and a length of 3000 mm, and a flexible tube constituting the guide tube 110 was configured from a PTFE tube having an inner diameter of 1.14 mm, an outer diameter of 1.59 mm, and a length of 700 mm. The length of a side hole region between two markers 113 was 100 mm. In this side hole region, as shown in the enlarged view in FIG. 8(B), nine side holes 112 having a diameter of 1.0 mm were arranged at constant intervals so as to open to the outside on alternately opposite sides. The distance between the centers of the holes in the side hole region was 10 mm. Furthermore, the distance between the side hole region and a connecting portion 111 was 300 mm.

Furthermore, in addition to this guide tube 110, a guide tube having a larger diameter was also manufactured. In this large-diameter guide tube, the inner diameter of the PTFE flexible tube was 1.33 mm, and the outer diameter was 1.93 mm.

Using the guide tube 110, an animal experiment was carried out as below. An endoscope was inserted through the mouth into the stomach of a female pig (body weight approximately 40 kg) under general anesthesia. The stomach was expanded through insufflation via the endoscope, and the endoscope was brought closer to the stomach wall at a point where the stomach wall and the abdominal wall were in contact with each other. The light from the endoscope was visually seen from the body surface. Toward the light, under observation using the endoscope, a puncture needle was caused to penetrate, from the body surface, the abdominal wall and the stomach wall, and was directly inserted into the stomach. Next, the guide tube 110 was inserted through the puncture needle into the stomach, and the tip portion 114 of the guide tube 110 was held by holding forceps inserted via an operation hole of the endoscope into the stomach. After part of the tip portion 114 was pulled into the endoscope and secured, the puncture needle was extracted from the abdominal wall, suction was performed using an endoscope in the stomach to reduce the pressure.

Under observation using the endoscope, the tip portion 114 of the guide tube 110 was pulled by the endoscope. Adjustment was performed such that the plurality of side holes 112 provided on the guide tube 110 were positioned in the peritoneal cavity, while checking with the endoscope that a distal-most marker 113 had entered the stomach.

Figure 9:
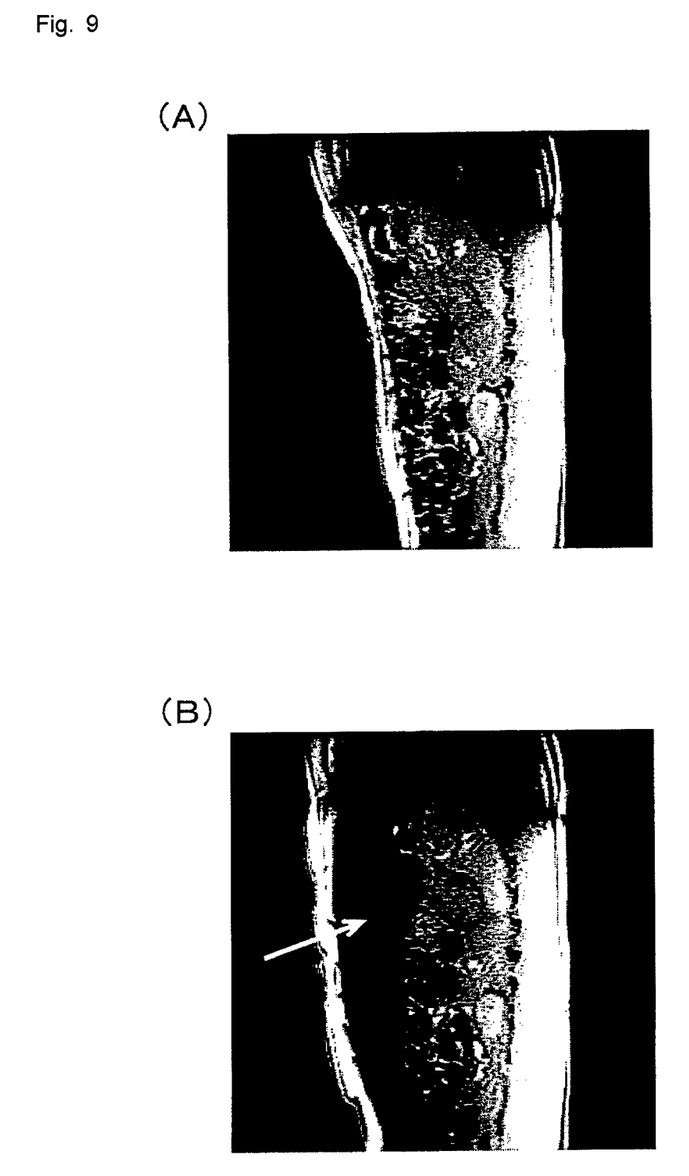
FIG. 9(A) is an image in magnetic resonance imaging (MRI) before injection of carbon dioxide.
FIG. 9(B) is an MRI image after the injection.

Next, the connecting portion 111 of the guide tube 110 was connected to a carbon dioxide insufflation apparatus, and carbon dioxide was injected from the side holes 112 of the guide tube 110 into the peritoneal cavity at a flow rate of 1 L/min. Expansion of the peritoneal cavity caused by the injection of carbon dioxide was visually seen, and the peritoneal cavity was imaged as an image in magnetic resonance imaging (MRI) using a nuclear magnetic resonance diagnostic device. FIGS. 9 (A) and 9(B) respectively show MRI images before and after injection of carbon dioxide. As seen from a comparison between FIG. 9 (A) before injection and FIG. 9(B) after injection, a pneumoperitoneum (the black portion indicated by the arrow in FIG. 9(B)) was formed.

INDUSTRIAL APPLICABILITY

According to the guide tube of the present invention, only with single puncture from the body surface into the lumen of a lumen organ, not only a preliminary pneumoperitoneum is formed, but the part of the lumen organ wall pierced during formation of the pneumoperitoneum can be used as a route for accessing the peritoneal cavity from the lumen of the lumen organ. According to the guide tube of the present invention, blind puncture into the peritoneal cavity is not performed, and, thus, damage to organs can be avoided. Almost all techniques are realized as simple operations that are the same as those in percutaneous endoscopic gastrostomy (PEG) already widely used in clinical practice, and, thus, a preliminary pneumoperitoneum can be safely and reliably created.

For example, the guide tube and the system of the present invention can be applied to creation of a route in transgastric NOTES. A transgastric route is a typical NOTES access route that is expected to be frequently used in diagnosis or procedure of abdominal or pelvic diseases. Specific application examples thereof include single puncture transgastric intraperitoneal exploration using an esophagogastroduodenoscope having a small diameter. It seems that the application can be made soon to progression degree evaluation on various malignant diseases, gynecological evaluation on tubal patency, liver biopsy, and the like. As a result, significant progress is made in introduction of NOTES to clinical practice.

The present invention can be widely applied not only to transgastric NOTES but also to general laparoscope techniques expected to enjoy advantages of the preliminary pneumoperitoneum method. Medically, there are cases in which puncture into the stomach under observation using an endoscope is considered to be safer than blind puncture into the peritoneal cavity. For such cases, a laparoscopic surgery can be also performed after safely creating a preliminary pneumoperitoneum using the guide tube of the present invention. In particular, the present invention is advantageous for patients who need to receive direct observation or procedure in the peritoneal cavity. In particular, in NOTES, which is a next-generation minimally-invasive technique, patients can return to the society soon, and an extremely large effect in the medical economy also can be expected.

DESCRIPTION OF THE REFERENCE SIGNS 10, 110 guide tube
11, 111 connecting portion
12, 112 side hole
13, 113 marker
14, 114 tip portion
20 endoscope
21 holding forceps
30 abdominal wall
40 stomach wall
50 peritoneal cavity
60 puncture needle

The invention claimed is:
1. A guide tube for forming a pneumoperitoneum comprising a flexible tube having an inner cavity,
 wherein the guide tube has an outer diameter that allows the guide tube to be inserted into a puncture needle having a size of 14 G to 18 G, a distal end of the guide tube is closed, and the distal end is provided with a wire that can be held by holding forceps provided in an endoscope and the wire has a length that allows the wire to be pulled into the endoscope, a proximal end of the flexible tube is provided with a connecting portion to an insufflation apparatus, and the flexible tube includes a side hole region having at least one side hole that can establish communication between the inner cavity of the flexible tube and outside the flexible tube in a case where the inner cavity is pressurized through insufflation, an insufflation source attached to the connecting portion and providing carbon dioxide to the at least one side hole, wherein the wire is located distal to the side hole region of the flexible tube, a proximal end of the wire is attached to the closed distal end of the flexible tube and a distal end of the wire projects distally beyond the distal end of the flexible tube, the wire is formed thinner than the flexible tube, and the length of the wire is 0.5 m to 5 m, and the length of the flexible tube is 0.3 m to 1.5 m.

2. The guide tube of claim 1, wherein an outer surface of the guide tube is provided with at least one marker.

3. The guide tube of claim 1, wherein an outer surface of the flexible tube is provided with markers at points of a distal side and a proximal side of the side hole region.

4. The guide tube of claim 1, wherein the side hole region has a length of 7 cm to 15 cm.

5. The guide tube of claim 1, wherein the wire has a diameter or width from 10 μm to 500 μm.

6. The guide tube of claim 1, wherein the wire is made of stainless steel.

7. The guide tube of claim 1, wherein the side hole region has two or more side holes and the side holes are arranged at intervals of 10 mm or more.

8. A system for forming a pneumoperitoneum, comprising:
the guide tube of claim 1; and
a puncture needle having a length that allows the puncture needle to penetrate a body surface into a target lumen.

9. The system for forming a pneumoperitoneum of claim 8, further comprising an insufflation apparatus.

10. The system for forming a pneumoperitoneum of claim 8, further comprising an endoscope, wherein the endoscope is provided at least with an observation optical system, an illumination optical system, holding forceps, and insufflation and suction apparatus.

11. The system for forming a pneumoperitoneum of claim 8, wherein the wire has a diameter or width from 10 μm to 500 μm.

12. The system for forming a pneumoperitoneum of claim 8, wherein the wire is made of stainless steel.

13. The system for forming a pneumoperitoneum of claim 8, wherein the side hole region has two or more side holes and the side holes are arranged at intervals of 10 mm or more.

* * * * *